United States Patent
Kothandaraman

(10) Patent No.: US 9,713,721 B2
(45) Date of Patent: Jul. 25, 2017

(54) SYSTEM AND METHOD FOR STORING APPLICATION SPECIFIC AND LEAD CONFIGURATION INFORMATION IN NEUROSTIMULATION DEVICE

(75) Inventor: Sridhar Kothandaraman, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1028 days.

(21) Appl. No.: 13/292,989

(22) Filed: Nov. 9, 2011

(65) Prior Publication Data

US 2012/0116476 A1   May 10, 2012

Related U.S. Application Data

(60) Provisional application No. 61/412,288, filed on Nov. 10, 2010.

(51) Int. Cl.
*A61N 1/36* (2006.01)
*A61N 1/372* (2006.01)
*G06F 19/00* (2011.01)

(52) U.S. Cl.
CPC ..... *A61N 1/36185* (2013.01); *A61N 1/37247* (2013.01); *G06F 19/3412* (2013.01); *A61N 1/36071* (2013.01); *A61N 1/37264* (2013.01)

(58) Field of Classification Search
CPC ............ A61N 1/36185; A61N 1/36071; A61N 1/37264
USPC .............................. 607/31, 45, 59
See application file for complete search history.

(56) References Cited

U.S. PATENT DOCUMENTS

| | | | |
|---|---|---|---|
| 6,308,099 B1 * | 10/2001 | Fox et al. | 607/31 |
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 7,317,948 B1 | 1/2008 | King et al. | |
| 7,805,197 B2 | 9/2010 | Bradley | |
| 8,131,357 B2 | 3/2012 | Bradley et al. | |
| 2006/0224222 A1 | 10/2006 | Bradley et al. | |
| 2007/0239228 A1 | 10/2007 | Bradley | |
| 2010/0010566 A1 | 1/2010 | Thacker et al. | |
| 2010/0121409 A1 | 5/2010 | Kothandaraman et al. | |
| 2010/0137944 A1 | 6/2010 | Zhu | |
| 2010/0331922 A1 | 12/2010 | DiGiore et al. | |
| 2011/0054551 A1 | 3/2011 | Zhu et al. | |
| 2011/0054567 A1 | 3/2011 | Lane et al. | |

(Continued)

OTHER PUBLICATIONS

U.S. Appl. No. 61/333,673, System and Method for Defining Neurostimulation Lead Configurations, Inventor: Sridhar Kothandaraman, filed May 11, 2010.

*Primary Examiner* — Michael D Abreu
(74) *Attorney, Agent, or Firm* — Schwegman Lundberg & Woessner, P.A.

(57) ABSTRACT

External control devices, neurostimulation systems, and programming methods. A neurostimulator includes a feature having a numerical range. Information identifying a type of the neurostimulator is transmitted to an external control device. The external control device receives the information from the neurostimulator, identifies the type of the neurostimulator based on the received information, and programs the neurostimulator in accordance with the numerical range of the feature corresponding to the identified type of the neurostimulator.

13 Claims, 9 Drawing Sheets

(56) References Cited

U.S. PATENT DOCUMENTS

2011/0054568 A1 3/2011 Lane et al.
2011/0054570 A1 3/2011 Lane

* cited by examiner

| IPG Type | # of Ports | # of Elec per Port | # of Timing Channels | # of Elec Per Timing Channel | # of Stim Programs | Pulse Amp Limit | Pulse Width Limit | Pulse Rate Limit |
|---|---|---|---|---|---|---|---|---|
| SCS | 2 | 8 | 4 | 16 | 4 | 0.1 ≤ x ≤ 10 | 10 ≤ x ≤ 1000 | 2 ≤ x ≤ 250 |
| DBS | 4 | 16 | 5 | 64 | 4 | 0.1 ≤ x ≤ 15 | 10 ≤ x ≤ 1000 | 2 ≤ x ≤ 2000 |
| PNS | 2 | 16 | 2 | 16 | 4 | 0.5 ≤ x ≤ 30 | 10 ≤ x ≤ 500 | 2 ≤ x ≤ 250 |
| ONS | 2 | 4 | 1 | 8 | 2 | 0.1 ≤ x ≤ 10 | 10 ≤ x ≤ 100 | 2 ≤ x ≤ 500 |
| FES | 1 | 8 | 1 | 8 | 1 | 0.1 ≤ x ≤ 10 | 10 ≤ x ≤ 100 | 2 ≤ x ≤ 500 |

FIG. 8

SYSTEM AND METHOD FOR STORING APPLICATION SPECIFIC AND LEAD CONFIGURATION INFORMATION IN NEUROSTIMULATION DEVICE

RELATED APPLICATION DATA

The present Application claims the benefit under 35 U.S.C. §119 to U.S. provisional patent application Ser. No. 61/412,288, filed Nov. 10, 2010. The foregoing application is hereby incorporated by reference into the present application in its entirety.

FIELD OF THE INVENTION

The present invention relates to tissue stimulation systems, and more particularly, to a system and method for programming an implantable neurostimulation device.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, Functional Electrical Stimulation (FES) systems such as the Freehand system by NeuroControl (Cleveland, Ohio) have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Occipital Nerve Stimulation (ONS), in which leads are implanted in the tissue over the occipital nerves, has shown promise as a treatment for various headaches, including migraine headaches, cluster headaches, and cervicogenic headaches.

These implantable neurostimulation systems typically include one or more electrode carrying neurostimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient.

The neurostimulation system may further comprise an external control device to remotely instruct the neurostimulator to generate electrical stimulation pulses in accordance with selected stimulation parameters. For example, the neurostimulation system may further comprise a handheld patient programmer in the form of a remote control (RC) to remotely instruct the neurostimulator to generate electrical stimulation pulses in accordance with the selected stimulation parameters. The RC may, itself, be programmed by a clinician, for example, by using a computerized programming system in the form of a clinician's programmer (CP), which typically includes a general purpose computer, such as a laptop, with a programming software package installed thereon.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width (or duration), and frequency (or rate) of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit, while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system, such as the afore-described CP. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets. The computerized programming system may be operated by a clinician attending the patient in several scenarios.

In order to achieve an effective result, the lead or leads must be placed in a location, such that the electrical stimulation will effectively treat the indentified disease or condition. If a lead is not correctly positioned, it is possible that the patient will receive little or no benefit from the implanted neurostimulator. Thus, correct lead placement can mean the difference between effective and ineffective pain therapy. When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the disease or condition. Thus, the navigation session may be used to pinpoint the stimulation region or areas correlating to the disease or condition. Such programming ability is particularly advantageous for targeting the tissue during implantation, or after implantation should the leads gradually or unexpectedly move that would otherwise relocate the stimulation energy away from the target site. By reprogramming the neurostimulator (typically by independently varying the stimulation energy on the electrodes), the stimulation region can often be moved back to the effective pain site without having to re-operate on the patient in order to reposition the lead and its electrode array.

It can be appreciated from this that the configuration of the leads (i.e., absolute and relative locations and orientation of the leads) is an important piece of information when programming a neurostimulator. This lead configuration information is typically readily available during implantation of the leads and is stored within the computerized programming system used during lead implantation in the OR. However, once implanted, subsequent programming of the neurostimulator requires this lead configuration information. Because the lead configuration information is only stored in the computerized programming system used in the OR, this same computerized programming system must be used during the navigation session or follow-up reprogramming session or the lead configuration information must be transferred from the OR computerized programming system to the new computerized programming system. However, in a clinical setting, it is quite common that the same computerized programming system is not available to program the neurostimulator, and there is a high likelihood that the neurostimulator is programmed or reprogrammed using a different computerized programming system (either in the same hospital/clinic or in a different hospital/clinic).

Stimulation applications, and thus the capabilities required to implement such applications, typically vary based on the clinical indications. However, the hardware contained in neurostimulators typically is designed to provide electrical stimulation capabilities that far exceed the requirements for the disease or condition for which it is intended to be used and is capable of being used for multiple clinical indications for widely different disease states. This is because most clinical indications share the same concepts and differ only by the numerical range of the features optimal for the particular clinical indication to be treated. The software and/or firmware contained in neurostimulators are typically designed to enable different ranges of features, depending upon the clinical indications for which they are intended to treat. As a result, different software packages for any particular computer programming system are typically required to respectively program the different types of neurostimulators. As such, multiple software packages must be loaded into a computerized programming system to provide it with the capability to program different types of neurostimulators, and if a computerized programming system in the field does not have the capability to program a particular neurostimulator type, the software package corresponding to that neurostimulator type must be ordered from the supplier and subsequently loaded into the computerized programming system. Furthermore, for each new type of neurostimulator that has been designed and released into the field, new programming software for the computerized programming system must be designed, tested (verification and validation), and released into the field.

There, thus, remains a need for an improved neurostimulator system that allows an external control device to program a neurostimulator implanted within a patient without having prior knowledge of the type of the neurostimulator and the configuration of the neurostimulation leads implanted within the patient.

SUMMARY OF THE INVENTION

In accordance with a first aspect of the present inventions, an external control device for use with a plurality of different types of programmable neurostimulators respectively having different numerical ranges for the same feature is provided. The different numerical ranges of the parameter may be, e.g., one of a different number of lead ports, a different number of electrodes supported by each port, a different number of timing channels, a different number of electrodes that can be programmed for each timing channel, a different number of stimulation programs, and different electrical stimulation parameter limit values.

The external control device comprises memory storing a software package capable of being selectively reconfigured to program each of the neurostimulators, and input circuitry configured for receiving information from one of the neurostimulators identifying the type of the one neurostimulator. In one embodiment, the memory stores the different numerical ranges of the parameter for the respective neurostimulators. In another embodiment, the input circuitry is configured for receiving the numerical range of the parameter from the one neurostimulator.

The external control device further comprises processing circuitry configured for identifying the type of the one neurostimulator based on the information received by the input circuitry and for configuring the software package, to program the one neurostimulator in accordance with the numerical range of the parameter corresponding to the identified type of the one neurostimulator. If the different numerical ranges of the parameter and the associate types of the neurostimulators are stored in the memory, they be stored in the form of a look-up table, in which case, the processing circuitry may be configured for accessing the look-up table, selecting the numerical range corresponding to the type of the one neurostimulator, and configuring the software package, to program the one neurostimulator in accordance with the selected numerical range.

In an optional embodiment, configured for generating display information identifying the type of the one neurostimulator based on the identified type of the one neurostimulator. For example, the display information may identify one of a neurostimulator type comprising a spinal cord stimulation (SCS) neurostimulator, a deep brain stimulation (DBS) neurostimulator, a peripheral nerve stimulation (PNS) neurostimulator, an occipital nerve stimulation (ONS) neurostimulator, and a Functional Electrical Stimulation (FES) neurostimulator. The external control device may comprise a housing containing the memory, input circuitry, and processing circuitry.

In accordance with a second aspect of the present inventions, a neurostimulation system is provided. The neurostimulation system comprises a neurostimulator including a feature having a numerical range (e.g., one of the numerical ranges set forth above), and configured for transmitting information identifying a type of the neurostimulator, and an external control device configured for receiving the information from the neurostimulator, identifying the type of the neurostimulator based on the received information, and programming the neurostimulator in accordance with the numerical range of the feature corresponding to the identified type of the neurostimulator.

In one embodiment, the external control device stores a plurality of different numerical ranges of the parameter and respective different types of neurostimulators associated with the different numerical ranges, and is configured for comparing the identified type of the neurostimulator with the stored different types of neurostimulators, selecting one of the different numerical ranges corresponding to the identified type of the neurostimulator based on the comparison, and programming the neurostimulator in accordance with the selected numerical range. In another embodiment, the neurostimulator is configured for transmitting the numerical range, and the external control device is configured for receiving the numerical range from the neurostimulator. In an optional embodiment, the external control device is configured for displaying information identifying the type of the neurostimulator (e.g., an SCS neurostimulator, a DBS neurostimulator, a PNS neurostimulator, an ONS neurostimulator, and an FES neurostimulator). The external control device may comprise a housing containing the memory, input circuitry, and processing circuitry.

In accordance with a third aspect of the present inventions, a method of programming one of a plurality of different types of programmable neurostimulators respectively having different numerical ranges for the parameter (e.g., one of the numerical ranges set forth above) is provided. The method comprises receiving information from the one neurostimulator identifying the type of the one neurostimulator, identifying the type of the one neurostimulator based on the received information, and programming the one neurostimulator in accordance with the numerical range of the parameter corresponding to the identified type of the one neurostimulator.

One method comprises accessing a look-up table storing the different numerical ranges of the parameter and the associated types of the neurostimulators, and selecting the numerical range corresponding to the type of the one neurostimulator, in which case, the neurostimulator is programmed in accordance with the selected numerical range. Another method further comprises receiving the numerical range of the parameter from the one neurostimulator. An optional method further comprises displaying information identifying the type of the one neurostimulator (e.g., an SCS neurostimulator, a DBS neurostimulator, a PNS neurostimulator, an ONS neurostimulator, and an FES neurostimulator) based on the identified type of the neurostimulator. Another optional method further comprises receiving information from another one of the neurostimulators identifying the type of the other neurostimulator, identifying the type of the other neurostimulator based on the received information, and programming the other neurostimulator in accordance with the numerical range of the parameter corresponding to the type of the other neurostimulator.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8 is a table setting forth IPG types and corresponding numerical ranges for IPG parameters;

DETAILED DESCRIPTION OF THE EMBODIMENTS

Figure 1:
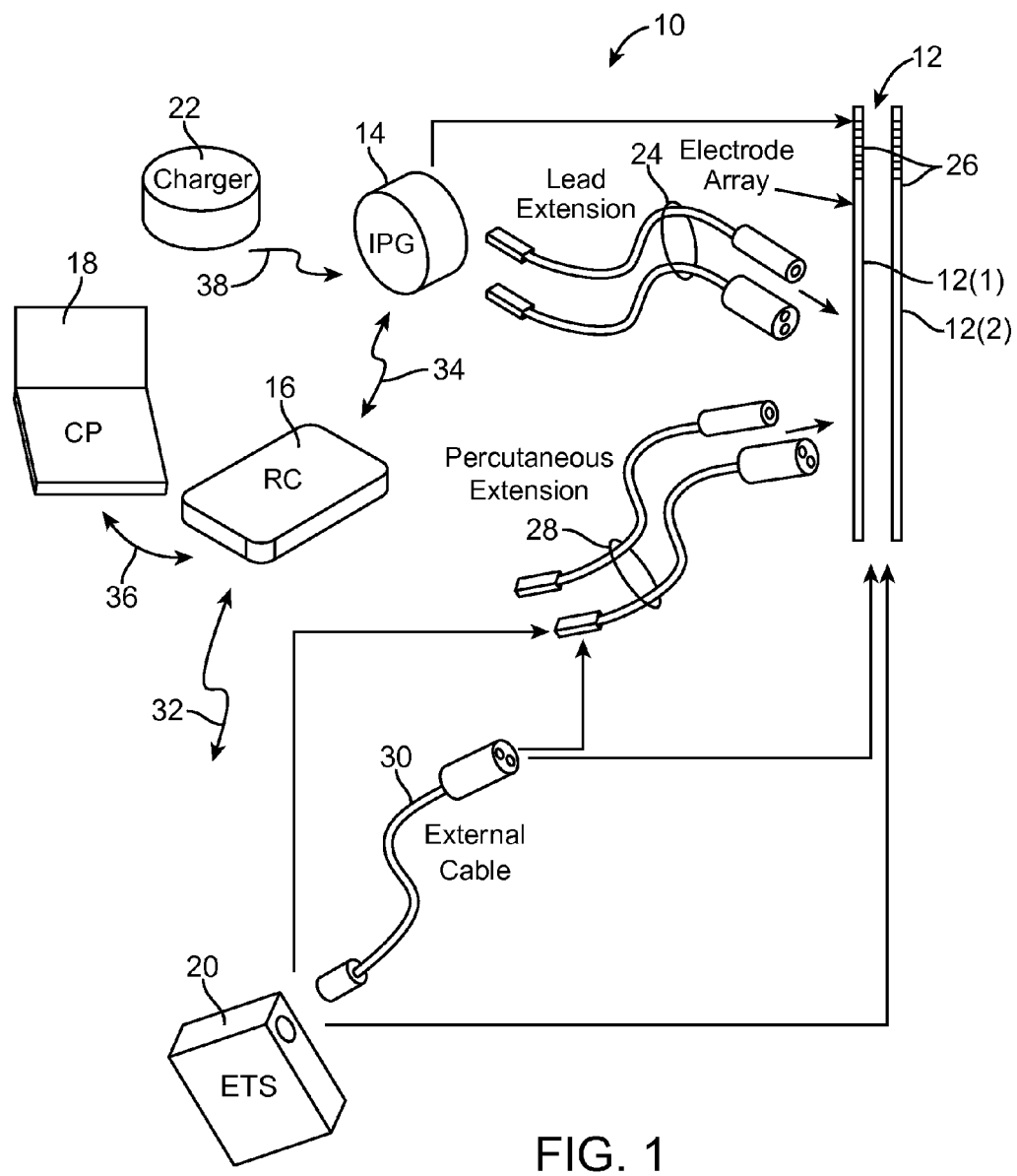
FIG. 1 is perspective view of one embodiment of a neurostimulation system arranged in accordance with the present inventions.

Turning first to FIG. 1, an exemplary configurable neurostimulation system 10 generally includes a plurality (in this case, two) of implantable neurostimulation leads 12, an implantable pulse generator (IPG) 14, an external remote controller RC 16, a clinician's programmer (CP) 18, an external trial stimulator (ETS) 20, and an external charger 22. As will be described in further detail below, the IPG 14 is selected from a plurality of different types of IPGs (e.g., a spinal cord stimulation (SCS) IPG, a deep brain stimulation (DBS) IPG, a peripheral nerve stimulation (PNS) IPG, an occipital nerve stimulation (ONS) IPG, and a Functional Electrical Stimulation (FES) IPG).

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14, through the RC 16, via an IR communications link 36. Alternatively, the CP 18 may directly communicate with the IPG 14 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
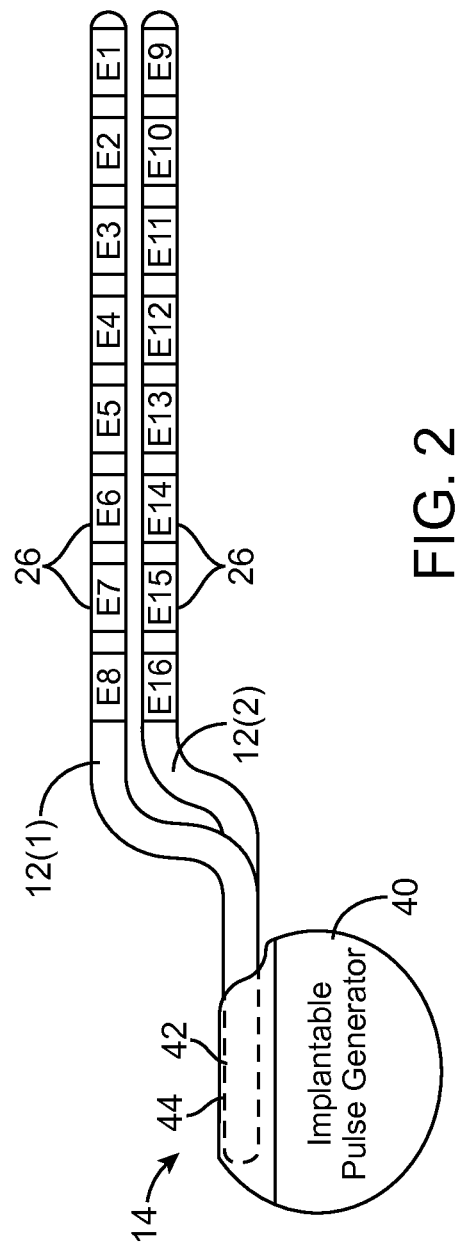
FIG. 2 is a side view of an implantable pulse generator and a pair of neurostimulation leads that can be used in the neurostimulation system of FIG. 1.

Referring now to FIG. 2, the external features of the neurostimulation leads 12 and the IPG 14 will be briefly described. One of the neurostimulation leads 12 has eight electrodes 26 (labeled E1-E8), and the other neurostimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the neurostimulation leads 12 mate in a manner that electrically couples the electrodes 26 to the internal electronics (described in further detail below) within the outer case 40. To this end, the connector 42 includes two ports 44 (only one shown in phantom) for receiving the proximal ends of the two neurostimulation leads 12. In the case where the lead extensions 24 are used, the ports 44 may instead receive the proximal ends of such lead extensions 24. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As briefly discussed above, the IPG 14 includes battery and pulse generation circuitry that delivers the electrical stimulation energy in the form of a pulsed electrical waveform to the electrode array 26 in accordance with a set of stimulation parameters programmed into the IPG 14. The IPG 14 may deliver different electrical pulsed waveforms over a plurality of timing channels, such that different regions of the patient can be treated with one stimulation program (i.e., a grouping of independent timing channels that can be operating simultaneously). In the IPG 14, up to four stimulation programs may be stored, with each stimulation program having four timing channels. Further details discussing the use of timing channels are described in U.S. patent application Ser. No. 11/399,876, entitled "System and Method Using Multiple Timing Channels for Electrode Adjustment During Set Up on an Implanted Stimulator Device," U.S. patent application Ser. No. 12/550,185, entitled "Methods to Avoid Frequency Locking in a Multi-Channel Neurostimulation System Using a Greatest Common Divisor Rule," U.S. patent application Ser. No. 12/550,237, entitled "Methods to Avoid Frequency Locking in a Multi-Channel Neurostimulation System Using Pulse Placement," and U.S. patent Ser. No. 12/550,213, entitled "Methods to Avoid Frequency Locking in a Multi-Channel Neurostimulation System Using Pulse Shifting," which are all expressly incorporated herein by reference.

For each timing channel, such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second), pulse shape, and burst rate (measured as the stimulation on duration per unit time).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and case 40. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 3:
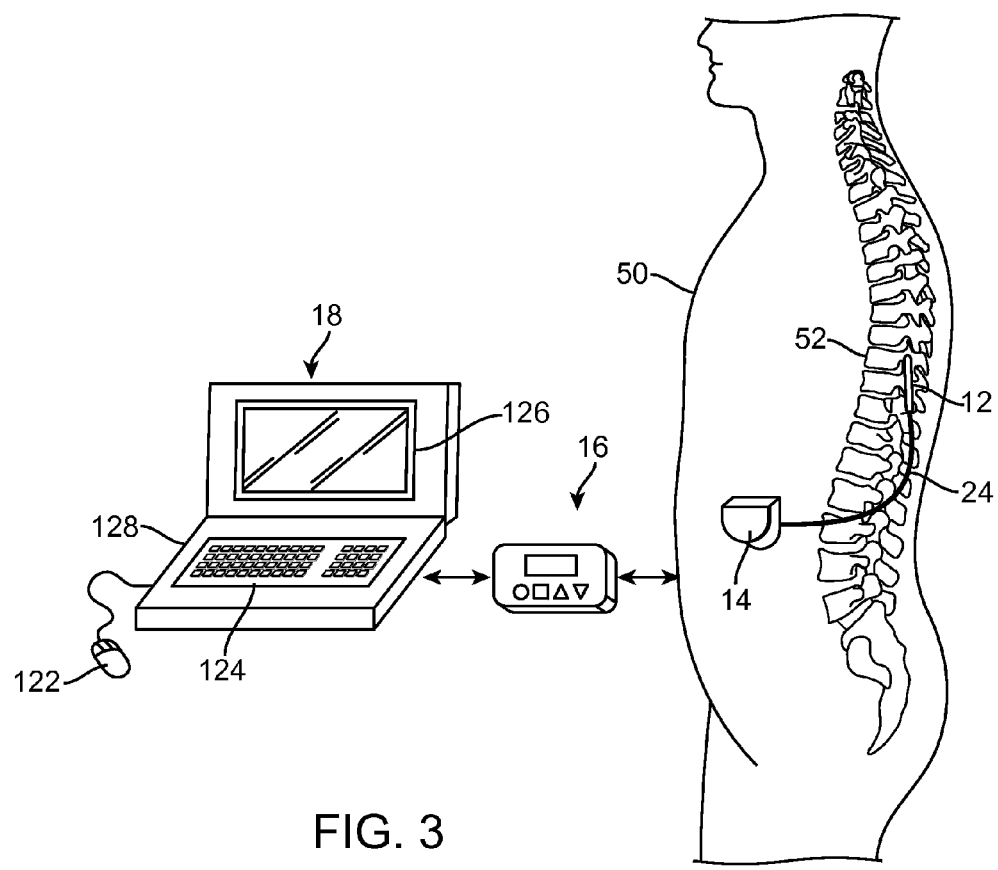
FIG. 3 is a plan view of the neurostimulation system of FIG. 1 in use with a patient.

As shown in FIG. 3, the neurostimulation leads 12 may be implanted within the spinal column 52 of a patient 50 in the case where the IPG 14 is of the type that can be used in spinal cord stimulation. Of course, for other clinical indications, the neurostimulation leads 12 may be implanted within other regions of the patient 50. For spinal cord stimulation, the preferred placement of the neurostimulation leads 12 is adjacent, i.e., resting near, or upon the dura, adjacent to the spinal cord area to be stimulated. Due to the lack of space near the location where the neurostimulation leads 12 exit the spinal column 52, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

As briefly discussed above, the IPG 14 may be selected from different types of IPGs. Each of the types of IPGs differs from at least one of the other types of IPGs by having different numerical ranges for a particular IPG parameter.

For example, the number of ports in two or more of the IPGs may differ from each other. The IPG 14 has two ports, but others of the IPGs may have, e.g., one, three, four etc. ports. The number of electrodes supported by each port in two or more of the IPGs may differ from each other. Each port 44 on the IPG 14 supports eight electrodes, but others of the IPGs may support, e.g., four, sixteen, etc. electrodes. The number of timing channels used by two or more of the IPGs may differ from each other. The IPG 14 uses four timing channels, but others of the IPGs may use e.g., one, two, three, five, etc. timing channels. The number of stimulation programs capable of being stored in two or more of the IPGs may differ from each other. Four stimulation programs may be stored in the IPG 14, although one, two, three, five, etc. stimulation programs may be stored in others of the IPGs. The number of electrodes that can be programmed for each timing channel for two or more of the IPGs may differ from each other. The IPG 14 can be programmed with sixteen electrodes for each of the timing channels, although two, four, eight, thirty-two, etc. electrodes can be programmed for each timing channel in other ones of the IPGs. The limit value or values of any one or more of the electrical stimulation parameters that can be programmed into any two or more of the IPGs may differ from each other. For the IPG 14, e.g., the pulse amplitude of the stimulation energy may have a lower limit value of 0.1 mA and an upper limit value of 10 mA, the pulse width may have a lower limit value of 10 μs and an upper limit value of 1000 μs, and the pulse rate may have a lower limit value of 2 pps and an upper limit value of 250 pps. The limit values for electrical stimulation parameters programmable into other ones of the IPGs may vary from these limit values.

Significantly, the neurostimulation system 10 is capable of providing a single software application that can program multiple types of IPGs 14 with different clinical indications, obviating the need to continually upgrade or install a new software application each time an IPG is developed or otherwise made available to the user.

In particular, the CP 18 is capable of reconfiguring itself to operate with any selected one of the IPG types. Specifically, the IPG 14 is configured for transmitting information identifying the type of the IPG 14 (e.g., the model number). Each time an IPG for a new clinical indication is designed, it may be enabled to transmit information identifying the IPG type. The CP 18 is configured for receiving the identifying information from the IPG 14 (or any other IPG type), identifying the type of the IPG 14 based on this information, and programming the IPG 14 in accordance with the numerical range of the IPG parameter corresponding to the identified type of the IPG 14.

In the case where the IPG 14 is to be programmed, the CP 18 will have knowledge, based on the communication from of the IPG type from the IPG 14, that the IPG 14 has two connector ports, four available timing channels, four stimulation programs, eight electrodes per port, a total of sixteen electrodes, and that the electrical stimulation parameters are limited to a pulse amplitude in the range of 0.1-10 mA, a pulse width in the range of 10 μs-1000 μs, and a pulse rate in the range of 2 pps-250 pps.

In one embodiment, the CP 18 stores a plurality of different numerical ranges for the IPG parameter and the respective different types of IPGs associated with the different numerical ranges. In this case, the CP 18 is configured for comparing the identified IPG type with the different IPG types stored in the CP 18, selecting the stored numerical range corresponding to the identified IPG type based on the comparison, and programming the IPG 14 in accordance with the selected numerical range.

In another embodiment, the IPG 14 is configured for transmitting the numerical range, in which case, the CP 18 is configured for receiving the numerical range from the IPG 14, and programming the IPG 14 in accordance with the numerical range received from the IPG 14. The advantage of this embodiment is that the CP 18 need not be updated with new numerical ranges for IPG parameters. Rather, as new IPG types with new numerical ranges for IPG parameters are developed, the numerical ranges can be stored within the new IPG type and transmitted to the CP 18 to enable subsequent programming of the new IPG in accordance with the numerical ranges.

The CP 18 may optionally display information identifying the IPG type (e.g., the CP 18 may display "SCS," indicating to the user that the IPG 14 is designed to perform spinal cord stimulation, "DBS," indicating to the user that the IPG 14 is designed to perform deep brain stimulation, "PNS," indicating that the IPG 14 is designed to perform peripheral nerve stimulation, "ONS," indicating that the IPG 14 is designed to perform occipital nerve stimulation," and "FES," indicating that the IPG 14 is designed to perform functional electrical stimulation.

The neurostimulation system 10 is also capable of programming or reprogramming the IPG 14 based on the implantation location of the neurostimulation leads 12 without having to use the device that initially programmed the IPG 14.

In particular, the IPG 14 is configured for acquiring lead configuration information defining the relative location between at least one of the neurostimulation leads 12 and a reference, which may, e.g., either be an anatomical reference (e.g., a vertebral level in the case of spinal cord stimulation) or the other neurostimulation lead 12 (e.g., a longitudinal stagger between the neurostimulation leads 12). The IPG 14 may acquire the lead configuration information from an external control device different from the CP 14 (e.g., during initial implantation of the IPG 14 and neurostimulation leads 12 within the patient) and store the lead configuration information in memory contained within the IPG 14. For example, the IPG 14 may measure data indicative of the location of one or both of the neurostimulation leads 12 relative to the reference, and the initial external control device may determine the lead configuration information based on this measured data. The initial external control device may then store this lead configuration information within the IPG 14, preferably in non-volatile memory. In a different embodiment, the lead configuration may be initially defined by a user via an external control device. For example, the user may view a fluoroscopic image of the leads 12 and surrounding tissue of the patient, and enter the lead configuration into the external control device, which can then store this lead configuration information within the IPG 14. In any event, once the lead configuration information has been stored in the IPG 14, the CP 14 may subsequently obtain the stored lead configuration from the IPG 14 and program the IPG 14 based on this lead configuration information.

Figure 4:
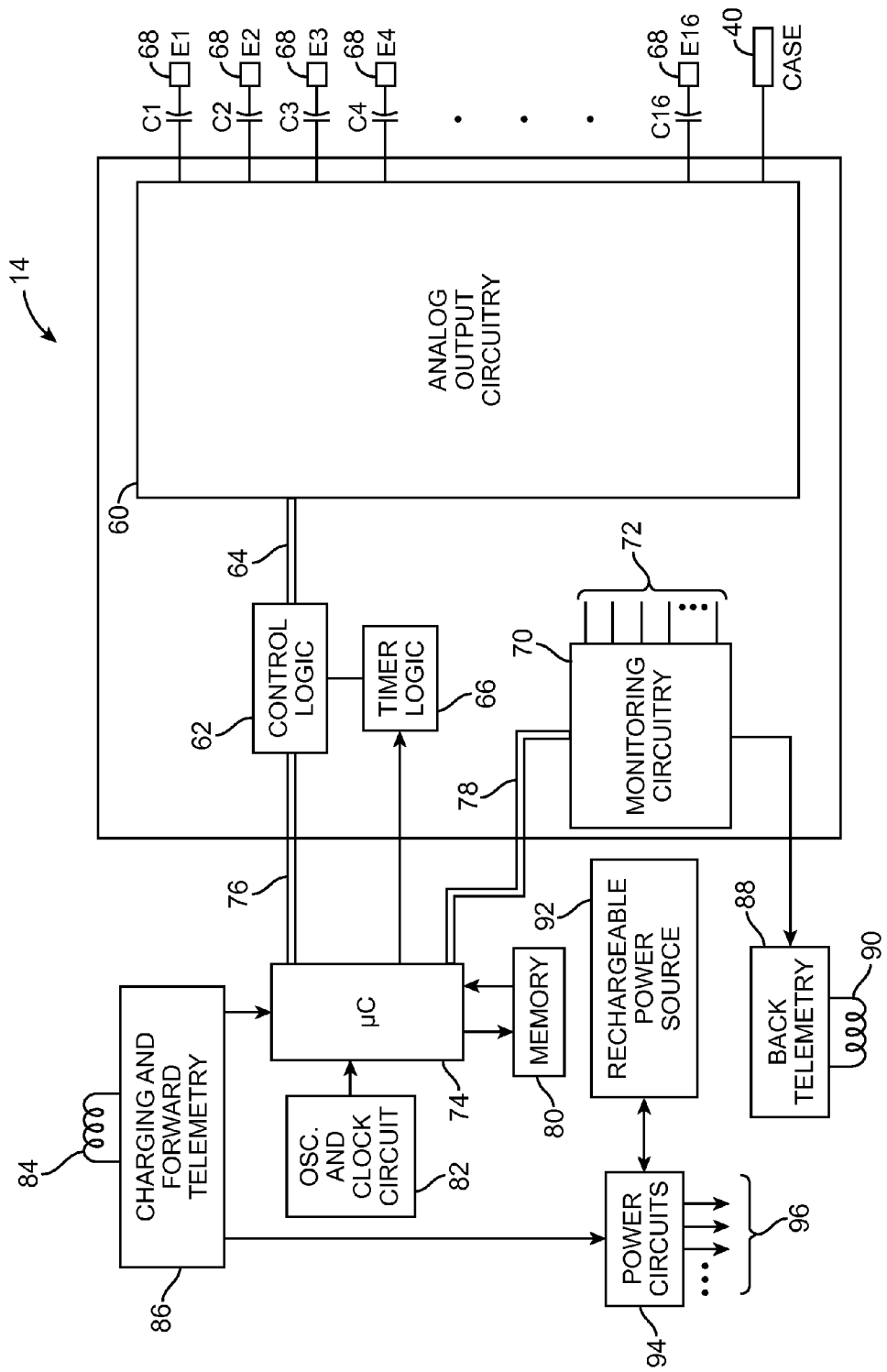
FIG. 4 is a block diagram of the internal componentry of the implantable pulse generator of FIG. 1.

Turning next to FIG. 4, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 µs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. Notably, the electrodes 26 fit snugly within the epidural space of the spinal column, and because the tissue is conductive, electrical measurements can be taken from the electrodes 26. Significantly, the monitoring circuitry 70 is configured for taking such electrical measurements, so that, as will be described in further detail below, the location of each of the leads 12 relative to the reference may be determined. In the illustrated embodiment, the electrical measurements taken by the monitoring circuitry 70 for the purpose of determining the relative locations of the leads 12 may be any suitable measurement, e.g., an electrical impedance, an electrical field potential, or an evoked potential measurement. The monitoring circuitry 70 may also measure impedance at each electrode 26 in order to determine the coupling efficiency between the respective electrode 26 and the tissue and/or to facilitate fault detection with respect to the connection between the electrodes 26 and the analog output circuitry 60 of the IPG 14.

Electrical data can be measured using any one of a variety means. For example, the electrical data measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference.

To facilitate determination of the location of each neurostimulation lead 12, electrical signals can be transmitted between electrodes carried by one of the neurostimulation lead 12 and one or more other electrodes (e.g., electrodes on the same neurostimulation lead 12, electrodes on the other neurostimulation lead 12, the case 40 of the IPG 12, or an electrode affixed to the tissue), and then electrical parameters can be measured in response to the transmission of the electrical signals. Alternatively, lead location can be monitored using other means, such as strain gauge elements or optical fibers/coherence sensors within the leads 12. The location of the neurostimulation lead 12 relative to the tissue can then be determined based on the measured electrical parameters in a conventional manner, such as, e.g., any one or more of the manners disclosed in U.S. patent application Ser. No. 11/096,483, entitled "Apparatus and Methods for Detecting Migration of Neurostimulation Leads," and U.S. patent application Ser. No. 12/495,442, entitled "System and Method for Compensating for Shifting of Neurostimulation Leads in a Patent," which are expressly incorporated herein by reference. The location of one neurostimulation lead 12 relative to the other neurostimulation lead 12 can be determined based on the measured electrical parameters in a conventional manner, such as, e.g., any one or more of the manner disclosed in U.S. Pat. No. 6,993,384, entitled "Apparatus and Method for Determining the Relative Position and Orientation of Neurostimulation Leads," U.S. patent application Ser. No. 12/550,136, entitled "Method and Apparatus for Determining Relative Positioning Between Neurostimulation Leads," and U.S. patent application Ser. No. 12/623,976, entitled "Method and Apparatus for Determining Relative Positioning Between Neurostimulation Leads," which are expressly incorporated herein by reference.

The IPG 14 further comprises processing circuitry in the form of a microcontroller 74 that controls the control logic 62 over data bus 76, and obtains status data from the monitoring circuitry 70 via data bus 78. The microcontroller 74 additionally controls the timer logic 66. The IPG 14 further comprises memory 80 and an oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided. The microcontroller 74 also stores and accesses lead configuration information, the type of the IPG 14 (e.g., SCS, DBS, PNS, ONS, FES, etc) and optionally numerical ranges for the IPG parameters within the memory 80. The microcontroller 74 also controls information that is transmitted from and received by the IPG 14 via telemetry circuitry (described below).

The IPG 14 further comprises an alternating current (AC) receiving coil 84 for receiving programming data (e.g., the operating program and/or stimulation parameters) from the RC 16 and/or CP 18 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14. In addition to programming data, lead configuration information (presumably transmitted from an external control device separate from the RC 16 and/or CP 18) received via the AC receiving coil 84 and forward telemetry circuitry 86 can be stored in the memory 80.

The IPG 14 further comprises back telemetry circuitry 88 and an alternating current (AC) transmission coil 90 for sending informational data sensed through the monitoring circuitry 70 (including the measured data that can be used to generate the lead configuration information) to the RC 16 and/or CP 18. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16 and/or CP 18, all programmable settings, including lead configuration information, stored within the IPG 14 may be uploaded to the RC 16 and/or CP 18 via the telemetry circuitry 88 and AC transmission coil 90.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits) received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described. It should be noted that rather than an IPG for the neurostimulator, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
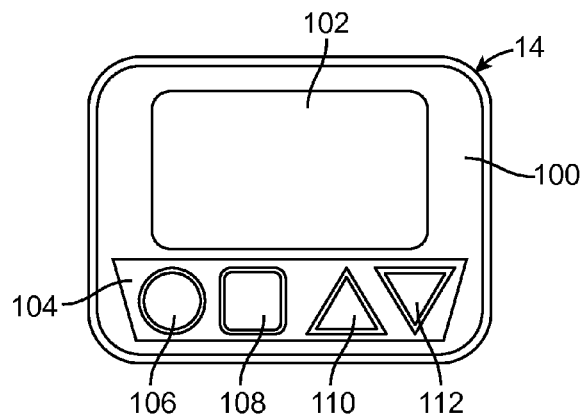
FIG. 5 is a plan view of a remote control that can be used in the neurostimulation system of FIG. 1.

Referring now to FIG. 5, one exemplary embodiment of an RC 16 will now be described. As previously discussed, the RC 16 is capable of communicating with the IPG 14 or CP 18. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touch-screen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 140N and OFF. The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate.

Figure 6:
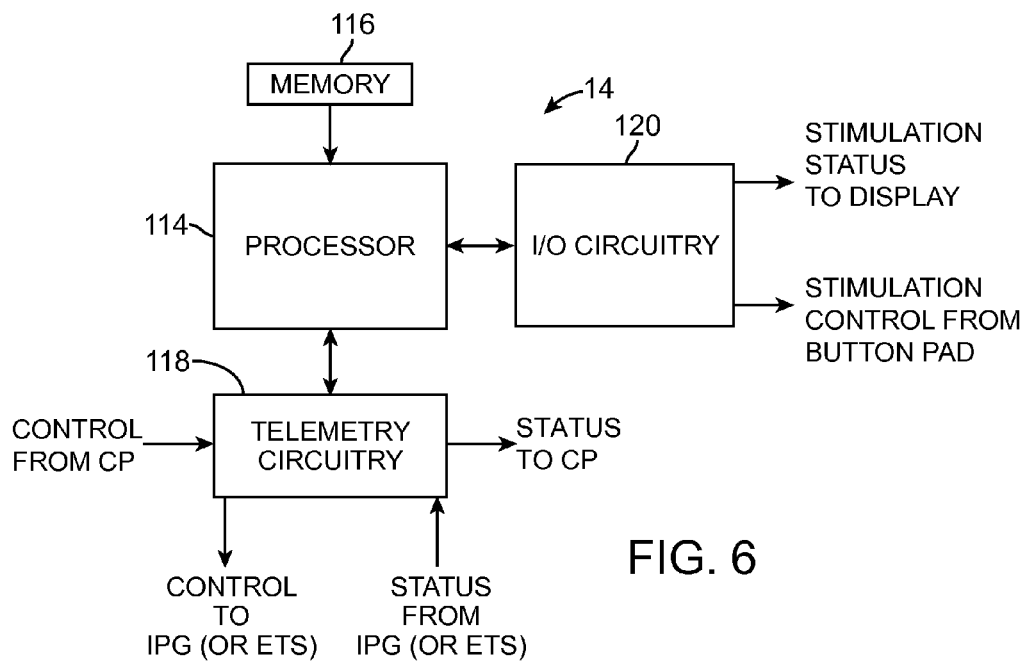
FIG. 6 is a block diagram of the internal componentry of the remote control of FIG. 5.

Referring to FIG. 6, the internal components of an exemplary RC 16 will now be described. The RC 16 generally includes a processor 114 (e.g., a microcontroller), memory 116 that stores an operating program for execution by the processor 114, and telemetry circuitry 118 for transmitting control data (including stimulation parameters and requests to provide status information) to the IPG 14 and receiving status information (including the measured electrical data) from the IPG 14 via link 34 (or link 32) (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the button pad 104 and transmitting status information to the display screen 102 (shown in FIG. 5). Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

To allow the clinician to perform these functions, the CP 18 includes a mouse 122, a keyboard 124, and a programming display screen 126 housed in a case 128. It is to be understood that in addition to, or in lieu of, the mouse 122, other directional programming devices may be used, such as a joystick, or directional keys included as part of the keys assigned to the keyboard 124.

Figure 7:
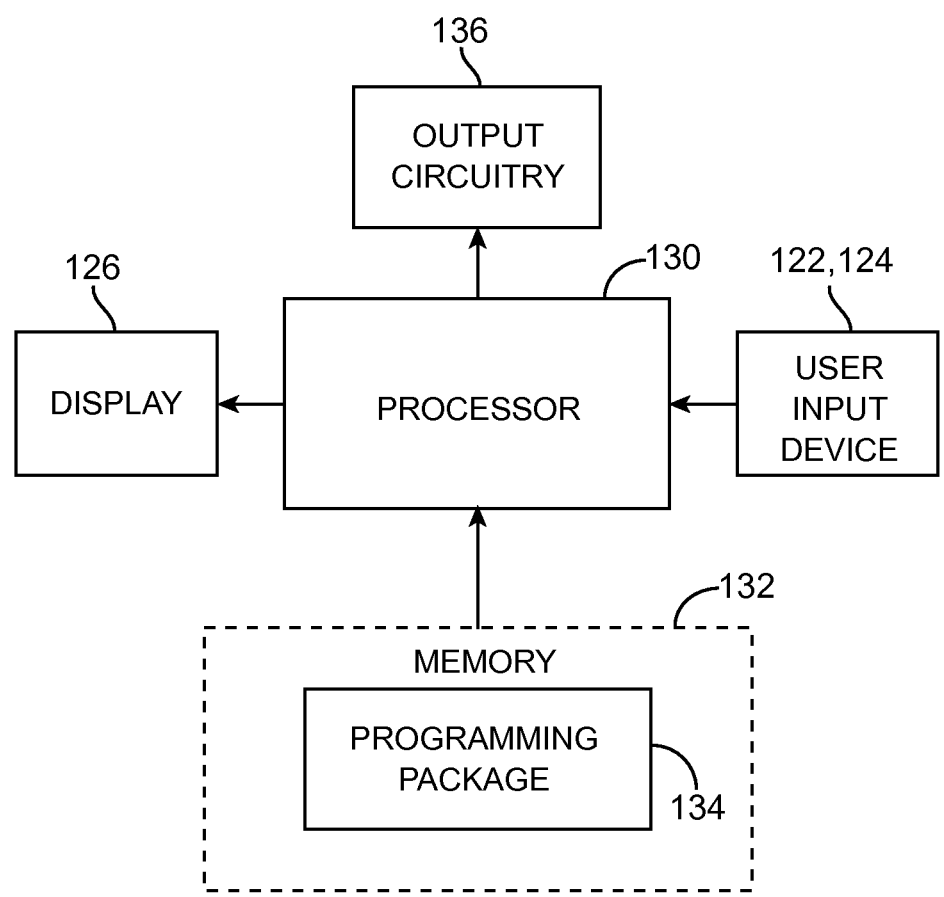
FIG. 7 is a block diagram of the components of a clinician programmer that can be used in the neurostimulation system of FIG. 1.

As shown in FIG. 7, the CP 18 generally includes a processor 130 (e.g., a central processor unit (CPU)) and memory 132 that stores a stimulation programming package 134, which can be executed by the processor 130 to allow a clinician to program the IPG 14 and RC 16. The memory 132 may optionally store different numerical ranges of a parameter and the associated types of IPGs, e.g., in the form of a look-up table. The CP 18 further includes telemetry circuitry 136 for downloading stimulation parameters to the RC 16 and uploading stimulation parameters already stored in the memory 116 of the RC 16 via link 36 (shown in FIG. 1). The telemetry circuitry 136 is also configured for transmitting the control data (including stimulation parameters and requests to provide status information) to the IPG 14 and receiving status information (including the measured electrical data, type of the IPG, and any numerical ranges of IPG parameters not already stored within the memory 132) from the IPG 14 indirectly via the RC 16.

Execution of the programming package 134 by the processor 130 provides a multitude of display screens (not shown) that can be navigated through via use of the mouse 122. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Significantly, the programming package 134 is reconfigurable in a manner that allows different types of IPGs to be programmed. To this end, the processor 130 is configured for identifying the type of IPG 14 based on the IPG type information received by the telemetry circuitry 136, and for configuring the programming package 134 to program the IPG 14 in accordance with the numerical range of the parameter corresponding to the identified type of the IPG 14. The processor 130 is optionally configured for generating display information identifying the type of the IPG 14 (in this case, SCS). In the advantageous case where the different numerical ranges for the different types of IPGs are stored in the memory 132 of the CP 18 in the form a look-up table, the processor 130 may access the look-up table, select the numerical range corresponding to the type of IPG 14, and configuring the software package, to program IPG 14 in accordance with the selected numerical range.

As one example, and with reference to FIG. 8, a look-up table contains a column of IPG types (in this case, SCS, DBS, PNS, ONS, and FES), and several columns of corresponding numerical ranges for different parameters (in this case, the number of lead ports, the number of electrodes supported by each port, the number of timing channels, the number of electrodes that can be programmed for each timing channel, the number of stimulation programs, and the electrical stimulation parameter limit values). In the case where the IPG 14 is designed to perform SCS, and therefore, sends information to the CP 18 identifying it as such, the processor 130 will select all of the numerical ranges corresponding to the SCS type and reconfigurable the programming package 134 in accordance with these numerical ranges.

Figure 9:
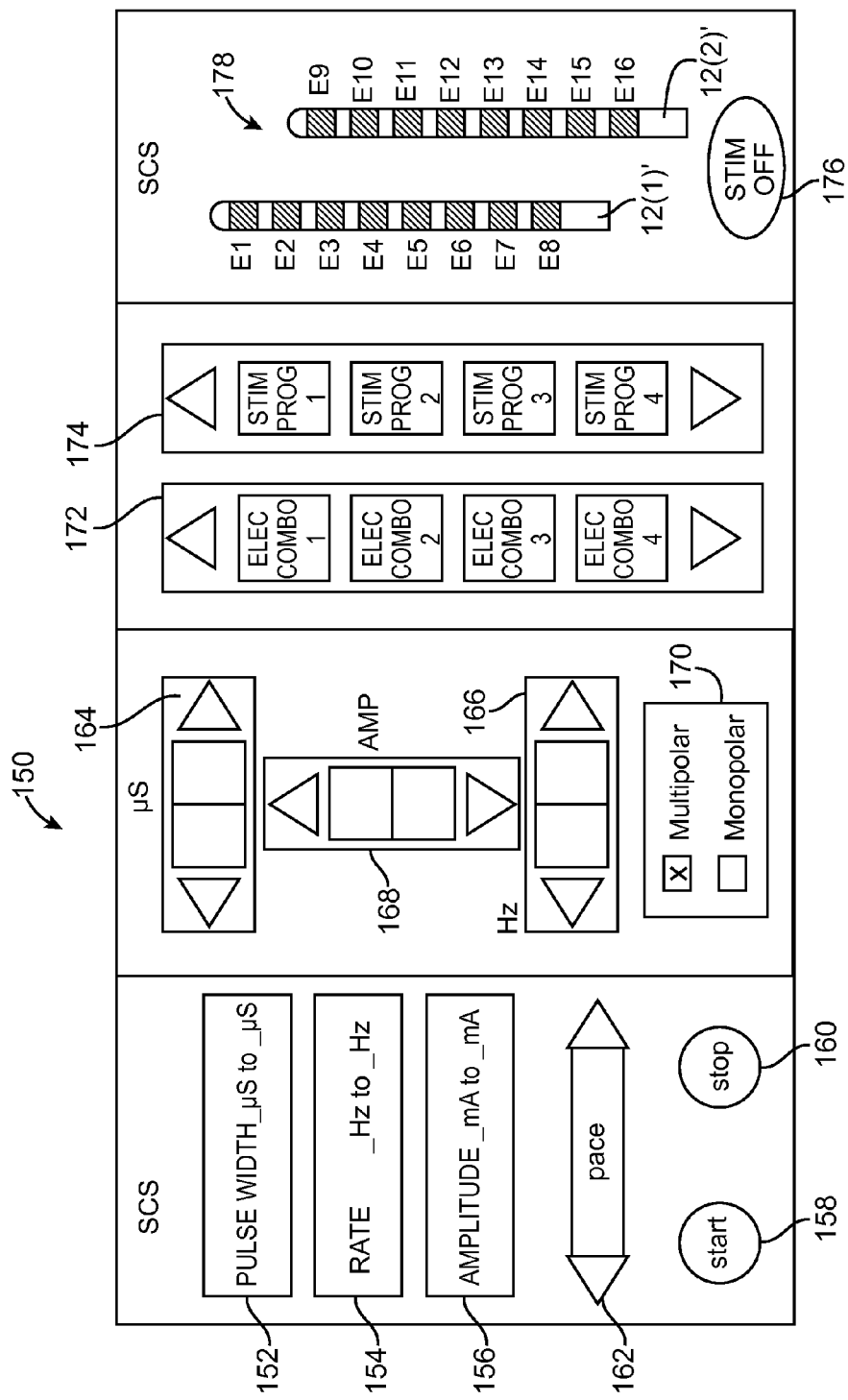
FIG. 9 is an illustration of a programming screen that can be displayed by the clinician programmer of FIG. 7.

An example of a programming screen 150 that can be generated by the CP 16 is shown in FIG. 9. The programming screen 150 allows a user to perform automated stimulation parameter testing, manual stimulation parameter testing, and electrode combination selection functions. The programming screen 150 includes an IPG type identifier (in this case, SCS) at the top, The programming screen 150 also includes various stimulation parameter entries that define the ranges of stimulation parameters to be automatically tested. In particular, the programming screen includes a pulse width entry 152 (expressed in microseconds (μs)), a pulse rate entry 154 (expressed in Hertz (Hz)), and a pulse amplitude entry 156 (expressed in milliamperes (mA)). The user may enter a "begin" value and an "end" value for each stimulation parameter to be automatically adjusted. The values of the pulse amplitude, pulse width, and pulse rate will be limited in accordance with the electrical stimulation parameter limit values stored in the IPG 14 and/or CP 18, such that the CP 18 will not allow the user to enter values outside of the allowed range. In one embodiment, only a single parameter (e.g., pulse width entry 154) is highlighted to be auto-adjusted. The programming screen 150 also includes a start button 158, which begins the automatic adjustment of the highlighted stimulation parameter from its "begin" value through a minimum increment to its "end" value, and a stop button 160, which halts the automatic adjustment of the highlighted stimulation parameter. The programming screen 150 also includes a pacing control 162, the left arrow of which can be clicked to decrease the speed of the parameter adjustment and the right arrow of which can be clicked to increase the speed of the parameter adjustment.

The programming screen 150 also includes various stimulation parameter controls that can be operated by the user to manually adjust stimulation parameters. In particular, the programming screen 150 includes a pulse width adjustment control 164 (expressed in microseconds (μs)), a pulse rate adjustment control 166 (expressed in Hertz (Hz)), and a pulse amplitude adjustment control 168 (expressed in milliamperes (mA)). Each control includes a first arrow that can be clicked to decrease the value of the respective stimulation parameter and a second arrow that can be clicked to increase the value of the respective stimulation parameter. The programming screen 150 also includes multipolar/monopolar stimulation selection control 170, which includes check boxes that can be alternately clicked by the user to provide multipolar or monopolar stimulation.

The programming screen 150 also includes an electrode combination control 172 having arrows that can be clicked by the user to select one of four different electrode combinations 1-4. Each of the electrode combinations 1-4 can be conventionally created either manually; for example, clicking on selected electrodes of a graphical electrode array (not shown) as anodes and cathodes and defining a percentage anodic current or cathodic current for each selected electrode (e.g., turning off electrode E1 as an anode, and turning on electrode E2 as an anode, and defining an anodic current for electrode E2), or automatically; for example, by gradually shifting current between anodic ones of the electrodes and/or gradually shifting current between cathodic ones of the electrodes via a directional device, such as a joystick or mouse (e.g., shifting anodic electrical current from electrode E1 to electrode E2 in 5% increments). A set of electrical stimulation parameters (pulse amplitude, pulse width, and pulse rate, as defined by the manual adjust stimulation parameters) is associated with each electrode combination.

The programming screen 150 also includes a stimulation program control 174 having arrows that can be clicked by the user to select one of four different stimulation programs 1-4. Each of the stimulation programs can be operated over four different timing channels for the respective four electrode combinations defined by the electrode combination control 172 and associated electrical stimulation parameters. As described above, although the number of stimulation programs is four and the number of electrode combinations (timing channels) is four in accordance with the SCS IPG, these numbers will vary based on the type of IPG. The programming screen 150 further includes a stimulation on/off control 176 that can be alternately clicked to turn the stimulation on or off.

Programming of the IPG 14 can be performed based on a neurostimulation lead configuration corresponding to the actual configuration in which the leads 12 are physically implanted within the patient. As discussed above, the CP 18 can obtain the neurostimulation lead configuration from the IPG 14 and display a graphical representation of a lead configuration 178 (i.e., a first virtual lead 12(1)' and second virtual lead 12(1)") that matches the actual configuration of the neurostimulation leads 12 implanted within the patient.

In this embodiment, the virtual leads 12' are displayed in a side-by-side arrangement that would presumably matches the side-by-side arrangement of the actual leads 12 implanted in the patient. In other embodiments, the virtual leads 12' may be displayed in a longitudinal arrangement (i.e., one lead completely above the other). Although the virtual leads 12' are illustrated as being superimposed on a blank background, the virtual leads 12' may be superimposed over a graphical representation of an anatomical region (e.g., the spine) at a location matching the location of the anatomical region at which the actual leads 12 are implanted. The virtual leads 12' may be adjusted by the user, e.g., using the techniques described in U.S. Provisional Patent Application Ser. No. 61/333,673, entitled "System and Method for Defining Neurostimulation Lead Configurations," which is expressly incorporated herein by reference.

Figure 10:
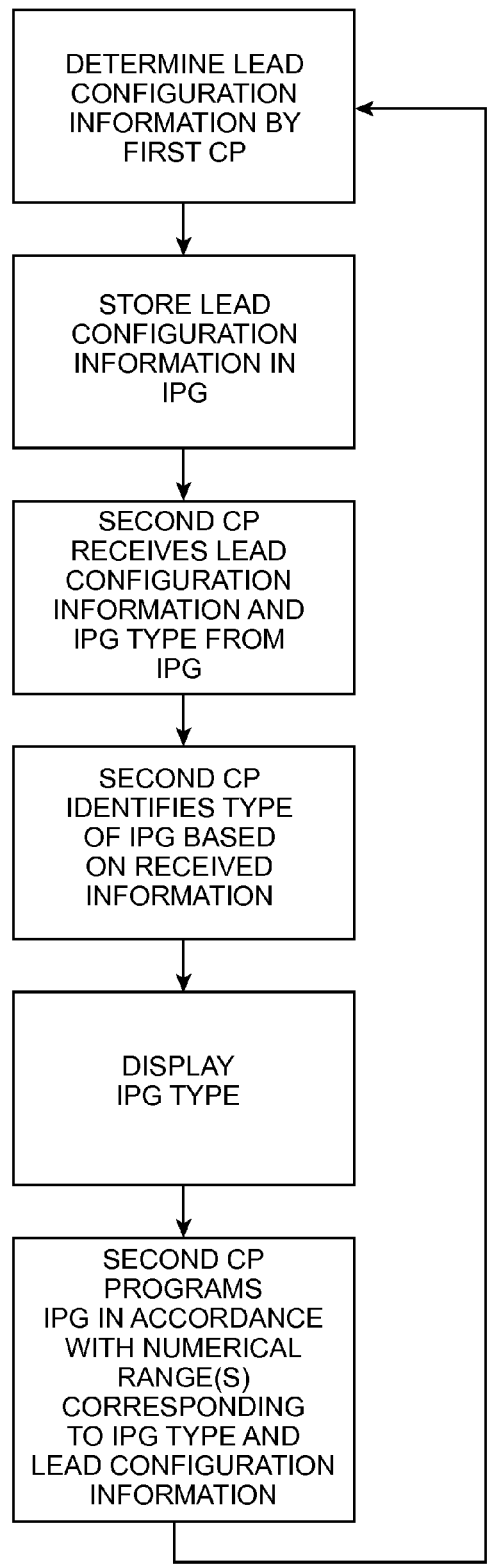
FIG. 10 is a flow diagram illustrating one method of programming the IPG of FIG. 2 in accordance with the present inventions.

Having described the arrangement and function of the components within the neurostimulation system 10, one method of programming the IPG 14 while coupled to two neurostimulation leads 12 implanted within a patient will now be described with respect to FIG. 10.

First, the configuration of the neurostimulation leads 12 either relative to an anatomical reference or relative to each other is determined automatically (measuring data at the IPG 14 and determining the lead configuration at a CP based on this measured data) or manually (e.g., viewing a fluoroscopic image and entering the lead configuration information in the CP 18) (step 200). Next, the lead configuration information is stored in the IPG 14, e.g., by transmitting the lead configuration information from the CP 18 to the IPG 14 (step 202). Presumably, these steps are performed during an OR mapping session, so that subsequent CPs are capable of interrogating the implanted IPG 14 for the lead configuration information.

Next, another CP receives from the IPG 14, lead configuration information and information identifying the type of the IPG 14 and any numerical ranges associated with that type of IPG (step 204). The other CP then identifies the type of the IPG 14 based on the information received from the IPG 14 (step 206), displays information identifying the type of the IPG (step 208), and programs the IPG 14, typically with user intervention, in accordance with lead configuration information and the numerical range (or ranges) of the parameter (or features) corresponding to the identified type of the IPG 14 (step 208). If the other CP stores a look-up table of different numerical ranges of the parameter (or features) and the associated types of IPGs, the other CP may select the numerical range (or ranges) corresponding to the identified type of the IPG, such that the IPG 14 can be programmed in accordance with this selected numerical range (or ranges). If the numerical range (or ranges) is supplied by the IPG 14, the other CP will simply use this numerical range (or ranges). Steps 200-208 can be repeated with a different type of IPG.

Although the IPG programming technique has been described as being implemented in the CP 18, it should be noted that this technique may be alternatively or additionally implemented in the RC 16.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external control device for use with a plurality of different types of programmable neurostimulators respectively having different numerical ranges for the same parameter, comprising:
   memory storing a software package capable of being selectively reconfigured to program each of the neurostimulators;
   input circuitry configured for receiving information from one of the neurostimulators identifying a type of the one neurostimulator; and
   processing circuitry configured for identifying the type of the one neurostimulator based on the information received by the input circuitry and for configuring the software package, to program the one neurostimulator in accordance with the numerical range of the parameter corresponding to the identified type of the one neurostimulator.

2. A neurostimulation system, comprising:
   a neurostimulator including a parameter having a numerical range, and configured for transmitting information identifying a type of the neurostimulator; and
   the external control device of claim 1.

3. The neurostimulation system of claim 2, wherein the external control device stores a plurality of different numerical ranges of the parameter and respective different types of neurostimulators associated with the different numerical ranges, and the external control device is configured for comparing the identified type of the neurostimulator with the stored different types of neurostimulators, selecting one of the different numerical ranges corresponding to the identified type of the neurostimulator based on the comparison, and programming the neurostimulator in accordance with the selected numerical range.

4. The neurostimulation system of claim 2, wherein the neurostimulator is configured for transmitting the numerical range, and the external control device is configured for receiving the numerical range from the neurostimulator.

5. The neurostimulation system of claim 2, wherein the numerical range is one of a number of lead ports, a number of electrodes supported by each port, a number of timing channels, a number of electrodes that can be programmed for each timing channel, a number of stimulation programs, and an electrical stimulation parameter limit value.

6. The neurostimulation system of claim 2, wherein the external control device is configured for displaying information identifying the type of the neurostimulator.

7. The external control device of claim 1, wherein the memory stores the different numerical ranges of the parameter for the respective neurostimulators.

8. The external control device of claim 7, wherein the different numerical ranges of the parameter and the associated types of the neurostimulators are stored in the memory in the form of a look-up table, and the processing circuitry is configured for accessing the look-up table, selecting the numerical range corresponding to the type of the one neurostimulator, and configuring the software package, to program the one neurostimulator in accordance with the selected numerical range.

9. The external control device of claim 1, wherein the processing circuitry is configured for generating display information identifying the type of the one neurostimulator based on the identified type of the one neurostimulator.

10. The external control device of claim 9, wherein the display information identifies one of a neurostimulator type comprising a spinal cord stimulation (SCS) neurostimulator, a deep brain stimulation (DBS) neurostimulator, a peripheral nerve stimulation (PNS) neurostimulator, an occipital nerve stimulation (ONS) neurostimulator, and a Functional Electrical Stimulation (FES) neurostimulator.

11. The external control device of claim 1, wherein the input circuitry is configured for receiving the numerical range of the parameter from the one neurostimulator.

12. The external control device of claim 1, wherein the different numerical ranges of the parameter is one of a different number of lead ports, a different number of electrodes supported by each port, a different number of timing channels, a different number of electrodes that can be programmed for each timing channel, a different number of stimulation programs, and different electrical stimulation parameter limit values.

13. The external control device of claim 1, further comprising a housing containing the memory, input circuitry, and processing circuitry.

* * * * *